United States Patent [19]

Dorman

[11] Patent Number: 5,079,467
[45] Date of Patent: Jan. 7, 1992

[54] RADIAL DRIVE FOR FLUID PUMP

[75] Inventor: Frank Dorman, Minneapolis, Minn.

[73] Assignee: Regents of the University of Minnesota, Minneapolis, Minn.

[21] Appl. No.: 603,525

[22] Filed: Oct. 15, 1990

Related U.S. Application Data

[62] Division of Ser. No. 377,273, Jul. 10, 1989.

[51] Int. Cl.[5] .............................................. H02K 1/06
[52] U.S. Cl. ................................... 310/156; 310/254; 310/179; 417/360
[58] Field of Search ............... 310/156, 254, 258, 259, 310/260, 270, 179, 182; 417/360, 423.9

[56] References Cited

U.S. PATENT DOCUMENTS

| | | | |
|---|---|---|---|
| 3,983,433 | 9/1976 | Sims | 310/254 |
| 4,874,975 | 10/1989 | Hertrich | 310/254 |
| 4,898,518 | 2/1990 | Hubbard et al. | 417/360 |

FOREIGN PATENT DOCUMENTS 017908  1/1987  United Kingdom ................ 310/254

Primary Examiner—William H. Beha, Jr.
Assistant Examiner—Matthew Nguyen
Attorney, Agent, or Firm—Frederick W. Niebuhr; John F. Thuente

[57] ABSTRACT

A centrifugal pump for left ventricle assist includes a pump housing forming an impeller chamber with inlet and outlet passages and enclosing an impeller rotatable to move blood or other fluids through the impeller chamber, and a rotor chamber enclosing a rotor integral with the impeller and rotatable to drive the impeller. A stator is mounted outside of a rotor casing forming the rotor chamber, concentric with, radially outward of and approximately axially aligned with the rotor. The stator includes a stator frame with an annular back iron and twenty-four teeth equally spaced apart and projected radially inwardly of the back iron. Three wires, one for each of three motor phases, are wound about the back iron, each including four symmetrically arranged active segments toroidally wound about the back iron, corresponding to four poles in a permanent magnet fixed to the rotor. Successive coils are wound in opposite toroidal directions, corresponding to an alternating and opposite arrangement of the poles of the magnet.

13 Claims, 4 Drawing Sheets

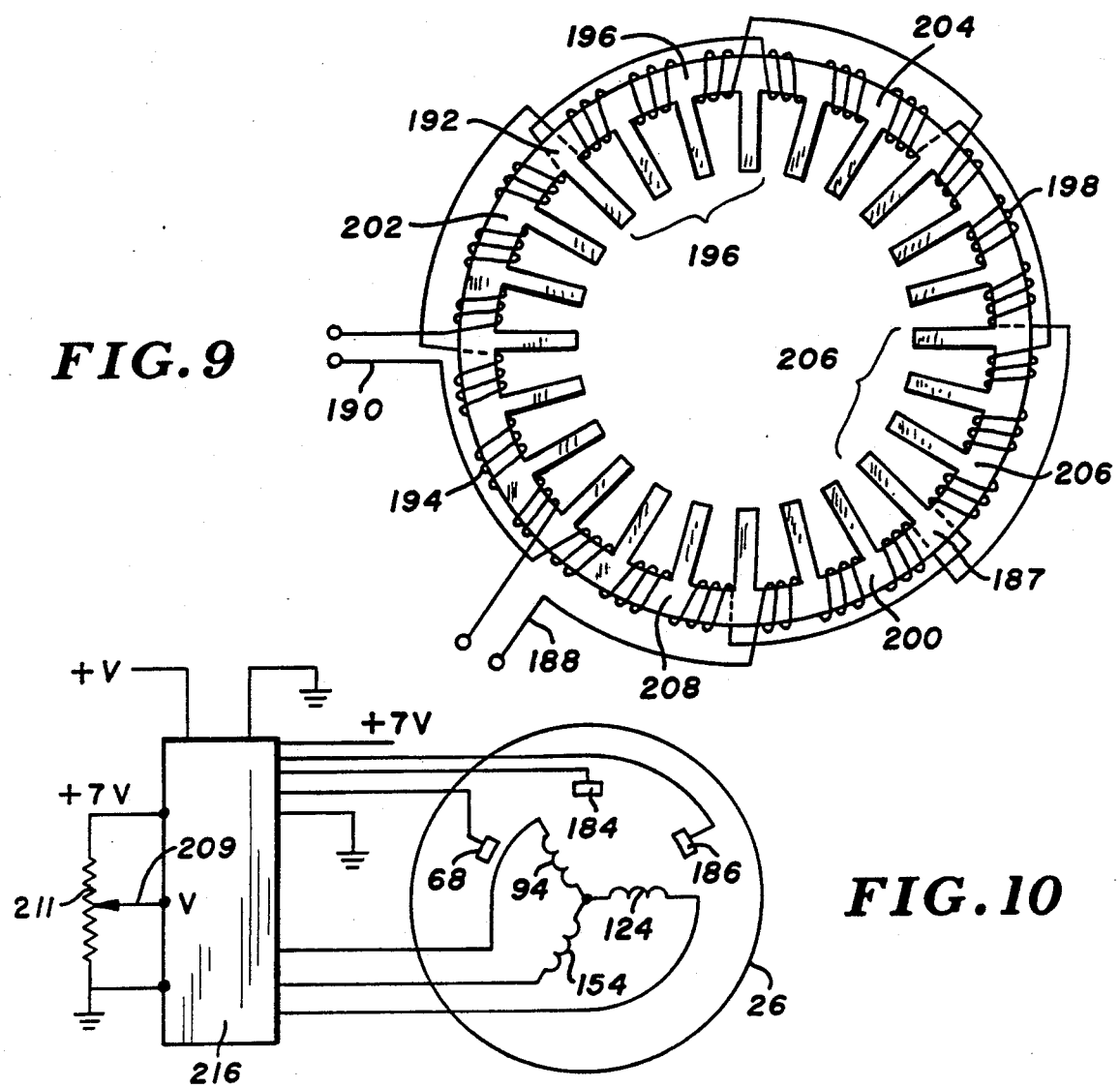
FIG.9
FIG.10
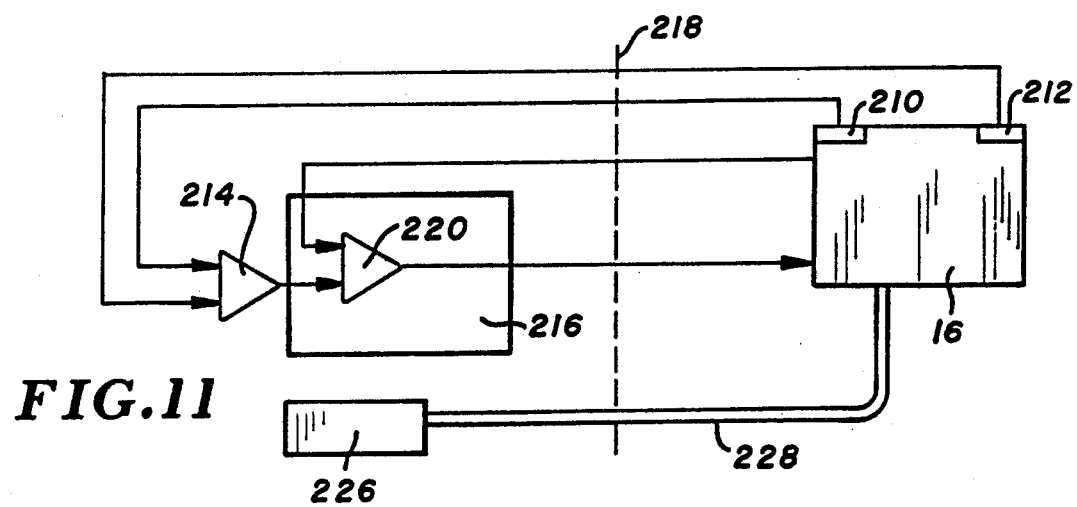
FIG.11

RADIAL DRIVE FOR FLUID PUMP

This is a divisional of copending application Ser. No. 07/377,273, filed on Jul. 10, 1989, in group.

BACKGROUND OF THE INVENTION

This invention relates to devices for conveying bodily fluids, and more particularly to body implantable left ventricle or whole-heart assist pumps for bypassing the heart during open heart surgery, or to assist a disfunctional heart or left ventricle. More particularly, this invention relates to a drive means suited for such pumps.

Centrifugal blood pumps have long been recognized for their utility as a supplement to or replacement for the human heart, for example in assisting a damaged left ventricle, for temporary heart bypass if required in open heart surgery, and for total heart bypass when two such pumps are implanted. Such pumps operate continuously and at high speeds, for example in the range of about 4,000 to 7,000 rpm, and are relatively small to facilitate implantation.

One of the more challenging aspects associated with body implantable centrifugal pumps is to provide an appropriate means for driving the impeller. One approach is noted in U. S. Pat. No. 4,135,253 (Reich et al), directed principally to the use of a saline solution as a fluid lubricant to float a pump rotor within a rotor housing. A two-pole permanent magnet is secured to the rotor, and another two-pole permanent magnet is outside the body, rotatable by a power supply also outside the body. The outside drive magnet is positioned against the skin, axially spaced apart from but coaxial with the pump rotor, whereby rotation of the drive magnet rotates the driven magnet in the rotor.

One difficulty encountered in this approach is a substantial normal or axial force between the drive magnet and driven magnet, resulting in unwanted pressure on the skin immediately over the implanted pump. Further due to the axial force, the rotor requires a high efficiency spiral groove thrust bearing formed on its surface facing a flat carbon thrust pad in the pump casing.

Accordingly, a radial coupling of drive and driven magnets would be desirable as virtually eliminating the axial force. This, however, would require the pump to form an outward bulge in the skin, sufficient to accommodate positioning of a radial driver. Even assuming a bulge of sufficient size, it would be difficult to position a radial driver concentrically with respect to the pump, resulting in unbalanced radial forces acting on the rotor.

Yet another challenge presented in the centrifugal pump design is to provide a drive means conforming to the pump geometry. In addition to the usual constraints upon the size of any drive means, there is a need for a radial coupling structure with a diameter over three times its axial length. This geometry tends to discourage use of a conventionally wound stator as a means to drive a rotor assembly including a permanent magnet, since conventionally wound coils would favor a stator having an axial length greater than its diameter. Finally, in any body implantable device there is a need to minimize, to the extent possible, heat generated by the rotor drive means, and to provide for effective dissipation of generated heat.

Therefore, it is an object of the present invention to provide a means for driving a body implantable centrifugal pump through a radial magnetic coupling between a stationary drive means and a movable rotor.

Another object is to provide a stationary rotor drive means including two or more electrically conductive coils for two or more phases of a motor comprised of the rotor and drive, with the coils wound in a manner to minimize heat generated during operation.

Another object is to provide a drive structure for a rotor that is particularly well suited for dissipation of heat generated during its operation and for precisely determining the radial gap between the rotor and drive.

Yet another object of the invention is to provide a drive apparatus surrounding a rotor and radially spaced apart from the rotor an adequate amount to permit a hydrodynamic bearing type support of the rotor within a centrifugal pump.

SUMMARY OF THE INVENTION

To achieve these and other objects, there is provided a pump drive motor including a rotor assembly with a permanent magnet having an equal number of North-magnetic and South-magnetic poles in an alternating configuration with opposite poles adjacent one another. A support means is provided for rotatably supporting the rotor assembly. Also provided is a stator including an annular stator frame coaxial with the rotor and fixed to the support means to provide a predetermined gap between the stator frame and rotor assembly. The stator frame is constructed of a magnetic flux carrying material and includes an annular outer rim having a diameter greater than the stator frame axial dimension. The stator further includes at least two electrical conductors disposed along the outer rim and electrically isolated from one another. Each conductor is formed into a series of active segments disposed circumferentially and symmetrically about the outer rim, and coupling segments between the active segments. Each active segment includes multiple traverses of the associated conductor, toroidally around the rim. Each coupling segment runs generally arcuately along the rim, in the form of a single strand or portion of the conductor. Consequently, the active segments have a length substantially greater than the length of the coupling segments. The active segments of each conductor are selectively angularly spaced apart from corresponding active segments of each of the other conductors. A drive means including an electrical power supply provides an electrical current to the conductors in a predetermined sequence to rotate the rotor assembly relative to the support means and stator.

Preferably the stator surrounds the rotor assembly in generally axially aligned and radially spaced apart relation thereto, to provide for a radial coupling of the rotor assembly and stator in which the predetermined gap is annular.

In one form of the invention, the stator frame has a plurality of teeth projected radially inwardly of the outer rim and spaced apart from one another to define a plurality of slots. The active segments of the conductors are disposed along the slots, with the number of slots being an integral multiple of the total number of active segments. Radially inward surfaces of the teeth cooperate to define a reference surface of the stator frame mounted contiguous with an exterior surface of the support means.

The stator frame is advantageously of laminar construction, including multiple sheets, e.g. ten or more, each with a thickness in the axial direction of less than about 0.02 inches. In a particularly preferred embodiment, twenty laminations, each 0.014 inches thick, are formed of a three percent silicon steel, a construction which minimizes eddy current loss.

One preferred construction forms a three-phase motor employing, as conductors, three insulated copper wire windings about the stator frame. Each of the coils includes four active segments, corresponding to four poles of the permanent magnet fixed within the rotor assembly. Further, the active segments of each coil are toroidally wound in opposite directions about the outer rim. Thus, with angularly adjacent active segments of the same coil are positioned near opposite poles of the permanent magnet, a cumulative force is provided for driving the rotor.

As compared to conventional windings of conductors about the stator frame, the windings in accordance with the present invention are well suited for body implantable devices, both in generating less heat for a particular drive torque and in more effective dissipation of generated heat. More particularly, the winding associated with each phase of the motor is shorter than a conventional winding about the teeth of the stator frame, yet generates sufficient torque due to the substantially larger length of the active segments as compared to the connecting segments of each conductor. The positioning of the conductors about the outer rim of the stator frame, rather than about the radially inward teeth, enhances dissipation of heat generated in the conductors. The inward edge surfaces project beyond the windings, and thus combine to provide a reference surface for mounting the stator frame to the centrifugal pump casing or other rotor support structure.

The radial coupling of the rotor and stator in accordance with the present invention, when used in combination with a centrifugal, body implantable pump, involves support of the rotor by the hydrodynamic bearing action of a saline fluid lubricant, which requires a predetermined gap between the rotor and stator frame having a radial dimension substantially larger, for example by an order of magnitude, than typical gaps between rotors and stators of similarly sized, conventional motors. The toroidal winding of the conductors, however, provides sufficient torque in spite of the relatively large gap to drive the motor at the required high speeds, for example 4,000 rpm or above.

Yet another feature of the present invention is the slightly axially offset alignment of the rotor and stator frame by virtue of a thrust bearing in the pump casing. In the absence of the thrust bearing, magnetic forces arising from the rotor magnets would tend to axially center the rotor within the stator frame. With radial centering provided by the journal bearing, the thrust bearing is positioned to engage the rotor to position the permanent magnet in a slightly axially offset position. Thus, the thrust bearing and magnetic forces act upon the rotor in opposite axial directions, tending to stabilize the rotor for proper functioning of the shaft lip seal and stable operation of the pump.

IN THE DRAWINGS

For a further understanding of the above and other features and advantages, reference is made to the following detailed description of the preferred embodiments and to the drawings, in which.

Figure 7:
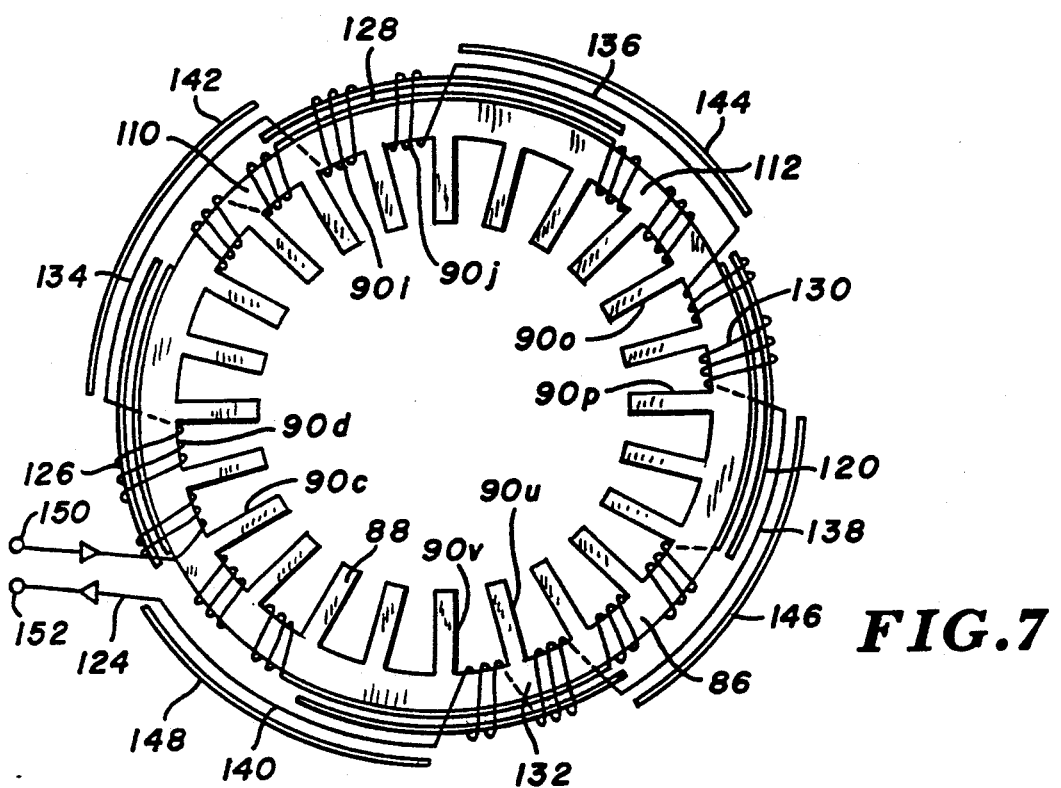
Figure 8:
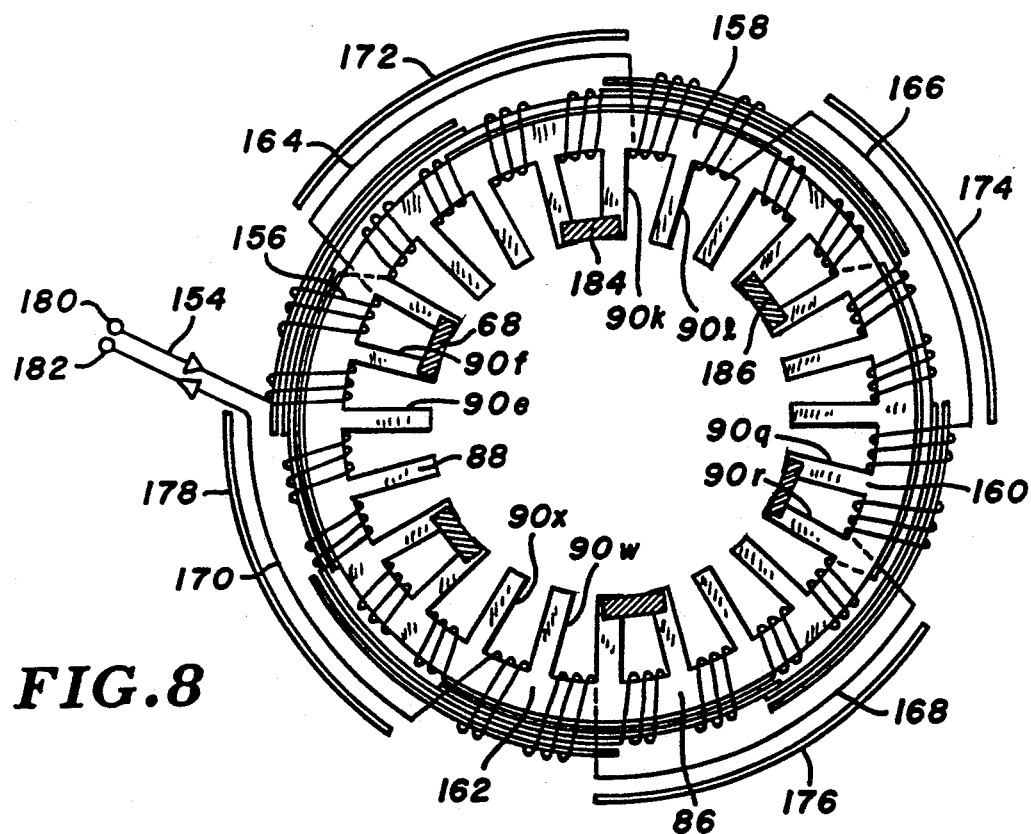

FIGS. 7 and 8 respectively illustrate second and final stages of winding conductors about the stator frame;

FIG. 9 is a plan view of a stator for an alternative embodiment centrifugal pump;

FIG. 10 is a schematic illustration of a brushless motor controller for the pump; and FIG. 11 is a diagrammatic view of an implanted pump and external control for operating the pump.

DETAILED DESCRIPTION OF THE PREFERRED EMBODIMENTS

Figure 1:
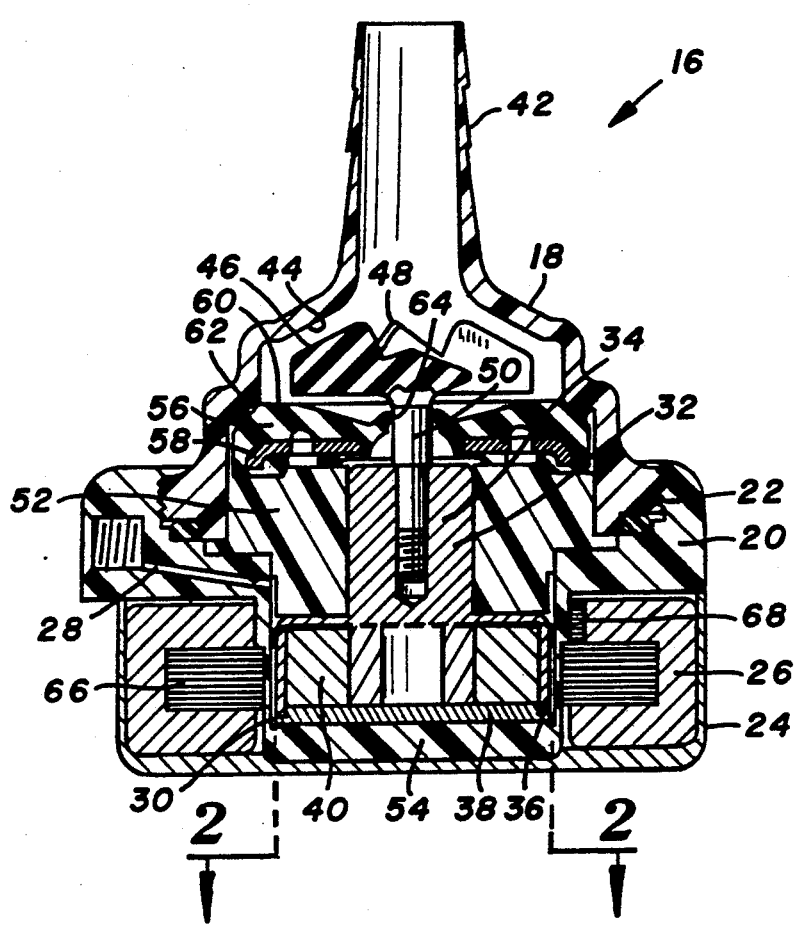
FIG. 1 is an elevational sectional view of a centrifugal pump constructed in accordance with the present invention.

Turning now to the drawings, there is shown in FIG. 1 a body implantable centrifugal pump 16, illustrated in sectional view to facilitate explanation of internal features. Pump 16 includes a dielectric housing formed by joinder of an impeller casing 18 and a rotor casing 20 at corresponding respective external and internal threaded portions indicated at 22. A titanium stator casing 24 surrounds the bottom portion of rotor casing 20, for securing an annular stator 26 to the outside of the rotor casing. Alternatively, the stator and rotor casing bottom portion can be encapsulated in a plastic, such as a biocompatible epoxy.

A saline solution or fluid lubricant is provided through a passageway 28 to a rotor chamber 30 formed by rotor casing 20. A stainless steel rotor 32 is contained to rotate within the chamber about a vertical axis, and is generally cylindrical having an inverted T-shaped profile. Rotor 32 includes a cylindrical shank 34 and a shell 36 below the shank and somewhat larger in diameter. A disc-shaped cover 38 is secured to the shell along the bottom, for enclosing an annular, four-pole neodymium iron (NdFe) permanent magnet 40. The magnet is sealed within the enclosure by welding cover 38, to separate the chemically reactive NdFe magnet from the saline solution, which prevents corrosion of the magnet and contamination of the solution. Magnet 40 also is cemented in place within the shell prior to welding of the cover to prevent free rotation of the magnet within the shell.

Impeller casing 18 includes an inlet throat 42 through which pump 16 receives blood or another bodily fluid. The casing forms an impeller chamber 44 in which an impeller 46 is rotatably mounted. More particularly, the impeller includes a plurality of impeller blades 48 fixed to a vertical cylindrical impeller shaft 50, which in turn is fixed to shank 34 either by a threaded connection or an adhesive, so that shaft 50 and impeller 46 are integral with rotor 32. The impeller, shaft and rotor further are concentric on a common axis of rotation which in FIG. 1 is vertical. Shaft 50 preferably is constructed of a low temperature isotropic graphite, or alternatively polished, stainless steel. Impeller 46 is constructed of polycarbonate or polysulfone.

The radial position of the rotor shaft impeller assembly, within and with respect to casings 18 and 20, is determined by an annular rotor guide 52 surrounding shank 34. Rotor guide 52 is fixed relative to the rotor casing, and preferably is constructed of polycarbonate or polysulfone, with an interior diameter slightly larger than the shank exterior diameter. The axial position of the rotor is limited by a thrust bearing 54 molded into rotor casing 20.

Impeller chamber 44 and rotor chamber 30 are separated from one another by a flexible annular seal member 56, preferably constructed of a graphite filled elastomer, e.g. neoprene rubber, with an embedded metal annular plate 58 for increased strength and stability. The upper surface of the seal facing the impeller chamber is provided with a non-thrombogenic polyurethane layer 60 to prevent formation of blood clots along the surface during pump operation. Seal member 56 includes a ring seal 62 and an annular lip seal 64 immediately surrounding shaft 50. For maximum seal effect at the lip seal and shaft interface, lip seal 64 and shaft 50 are concentric.

Rotor casing 20 is formed in the shape of a cup, with a cylindrical wall surrounding shell 36 preferably as thin as possible, while of course maintaining structural integrity, to minimize the radial gap between magnet 40 and stator 26, which is fixed to the rotor casing. The rotor casing is constructed of a dielectric material and thus does not allow formation of lossy eddy currents as a result of the magnetic field.

Stator 26 surrounds the lower portion of rotor casing 20 and is maintained in position by stator casing 24, positioned for a rotary magnetic coupling with magnet 40 in the rotor shell. The stator includes an annular frame or core 66 and a series of insulated copper wire windings about the core. Electrical energy is selectively supplied to the windings, to generate and alter the magnetic field between the stator and magnet to rotate magnet 40, and thus the rotor, impeller and shaft, at a predetermined speed, e.g. in the range of about 4,000 to 7,000 rpm. A plurality of Hall effect semiconductor elements, one of which is shown at 68, are mounted to stator frame 66 and respond to the polarity and strength of the magnetic field between the rotor and stator, to determine the angular position of the rotor with respect to the stator.

Operation of pump 16 involves two fluid paths. The first concerns passage of blood through inlet throat 42 into the impeller chamber, where it is expelled from the chamber through an exit conduit (not shown) due to rotation of impeller 46. The second fluid path involves the constant flow of the saline solution into rotor chamber 30 through passageway 28. In filling the rotor chamber, the saline solution provides a fluid lubricant between the moving rotor and shaft, and the fixed rotor casing, rotor guide and seal member. In particular, the solution provides hydrodynamic bearing action between the stationary and rotating parts in the form of thrust bearing interfaces between cover 38 and thrust bearing 54, and between rotor guide 52 and shell 36, and journal bearings between the rotor guide and shank 34, and also between shell 36 and the rotor casing. Finally, the saline solution forms an annular journal bearing between impeller shaft 50 and lip seal 64.

In addition to hydrodynamic bearing action, the saline fluid lubricant carries away heat generated by viscous losses, takes into solution any small air bubbles trapped in the rotor chamber, and perfuses into impeller chamber 44, thus to flush seal member 56 of any blood proteins or cells near the interface between the shaft and lip seal. For a further explanation of the centrifugal pump, reference is made to U.S. Pat. No. 4,927,407 (Dorman), assigned to the assignee of this application.

Figure 2:
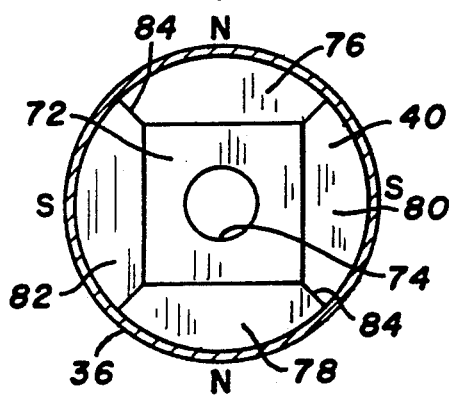
FIG. 2 is a plan view of a permanent magnet employed in a rotor of the centrifugal pump.

As seen in FIG. 2, permanent magnet 40 includes a soft iron central core 72 which is square in cross-section and has a central opening 74. Surrounding core 72 are four equally sized poles or quadrants, two at 76 and 78 being N-magnetic poles and two at 80 and 82 being S-magnetic poles, for an alternating arrangement in which neighboring poles are opposite. Poles 76-82 are constructed of a permanent magnet material identified as "MG 1" and available from the Delco Remy Division of General Motors, Anderson, Ind. The pole material is selected such that the magnetic flux density in the stator is kept below the saturation level to minimize hysteresis losses.

The use of four poles, rather than the six or eight poles typical for a rotor of this size, provides a comparatively longer pole length along the magnet circumference, to compensate for flux leakage at the junctions between adjacent poles Conversely, the use of four poles rather than two results in reduced maximum flux between poles along flux paths in the stator.

Pole quadrants 76-82 are cemented together with an epoxy, to provide radially extended gaps 84 between adjacent quadrants, and then ground about the periphery to provide a close fit within shell 36. Magnet 40 then is cemented in the shell with the epoxy, whereupon cover 38 is welded to the shell to seal the magnet.

Figure 3:
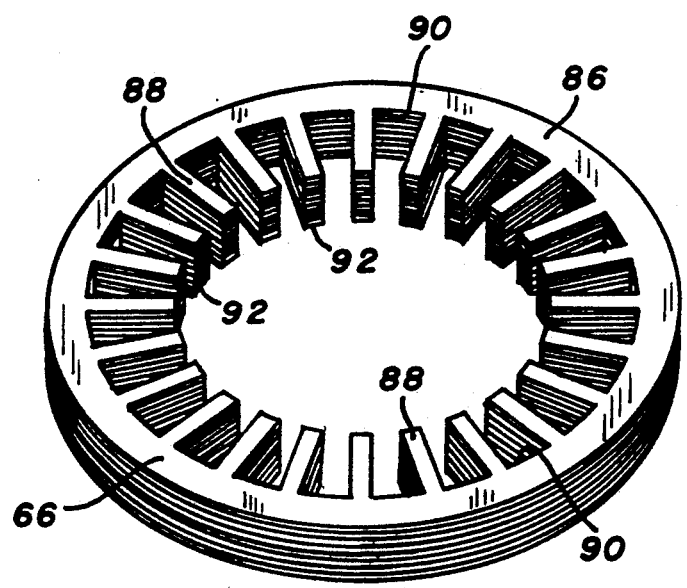
FIG. 3 is a perspective view of a stator frame employed in the centrifugal pump.
Figure 4:
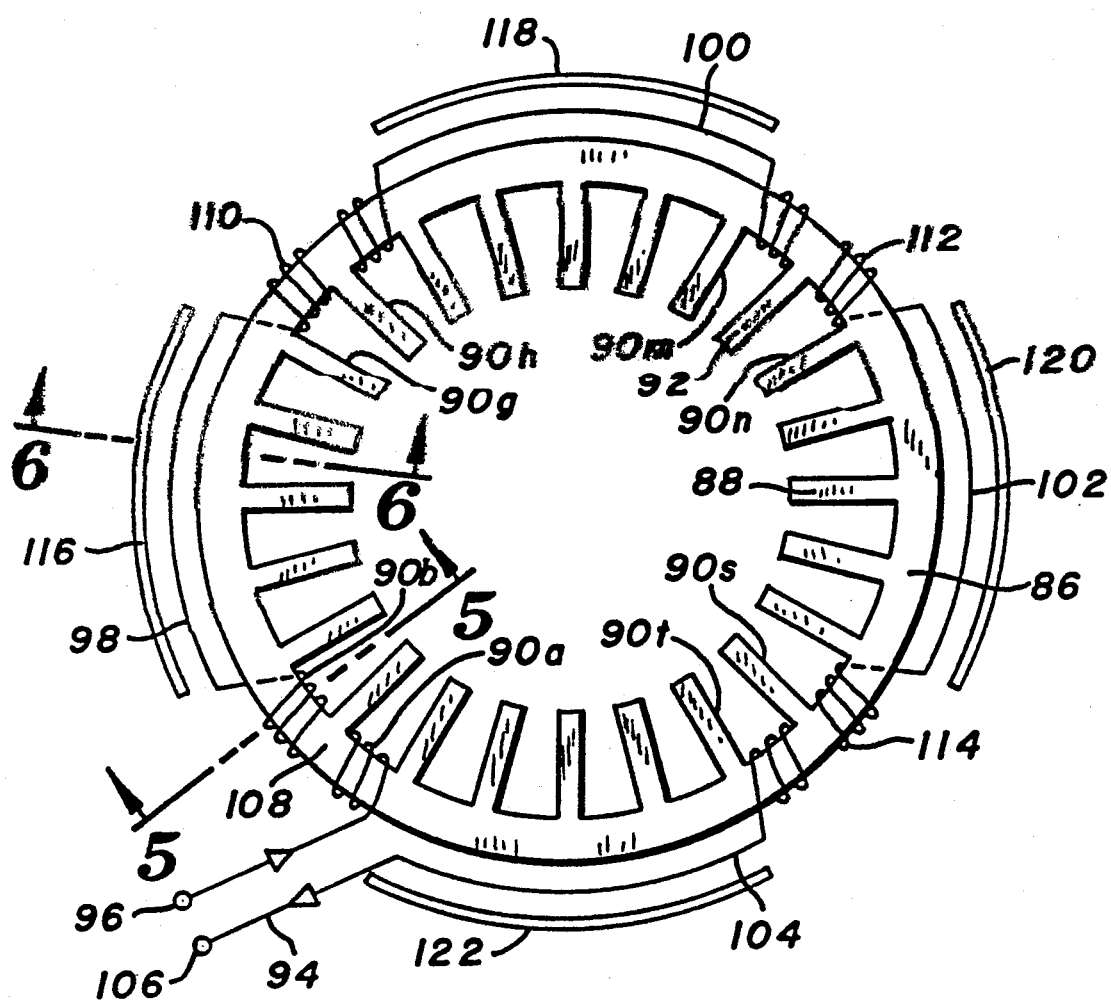
FIG. 4 is a plan view illustrating a first step in winding electrical conductors about the stator frame.
Figure 5:
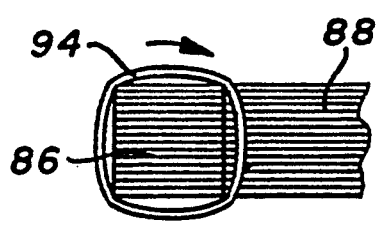
FIG. 5 is a sectional view taken along the line 5—5 in FIG. 4.

In FIG. 3, stator frame or core 66 is shown separately to reveal certain structural features including an annular back iron or outer rim 86 and a series of twenty-four teeth 88 projected radially inwardly of the outer rim. Teeth 88 are of equal size and shape, and angularly spaced apart an equal distance from one another to form a series of twenty-four slots 90 between the teeth. The radially inward edge surfaces 92 of teeth 88 cooperate to form a cylindrical reference surface that is contiguous with the outside wall of rotor casing 20 in the assembled pump.

Stator frame 66 preferably is of laminar construction, in one preferred example consisting of a stack of twenty sheets of a low magnetic reluctance material, e.g. M19 grade silicone steel (three percent silicone), with each sheet having a thickness of 0.14 inches. The sheets or laminations are each coated with a thin insulative oxide film, then assembled into the twenty sheet stack, with the assembly then coated with a conforming layer of epoxy insulation, over all surfaces except the inside edges 92 of teeth 88.

The assembly of stator 26 is illustrated in FIGS. 4–8, and involves winding three copper wires around back iron 86 of the stator frame, in a manner to electrically isolate the individual wires from one another and form three separate conductive paths, one associated with each of three phases of the motor formed by the rotor and stator.

In a first stage of assembly, a copper wire 94 from a terminal 96 is wound about rim 86 in slot 90a in a toroidal pattern including a selected number of turns, in the present example thirty turns of number 24 AWG wire, then similarly wound in slot 90b, i.e. toroidally in the same direction and with the same number of turns. Wire 94 proceeds arcuately along the outer rim as indicated at 98, to slots 90g and 90h, where it is wound about the outer rim in a fashion somewhat similar to the windings along slots 90a and 90b. A critical difference, however, is that the toroidal windings are in the opposite direction, i.e. radially outward across the top of rim 86 as the winding proceeds clockwise along the top of the rim, as opposed to radially inward across the top for slots 90a and 90b. A coupling segment 100 of the wire proceeds arcuately along the outer rim to slots 90m and 90n, where the wire is wound in the manner and direction of the windings at slots 90a and 90b. Then, a coupling segment 102 proceeds arcuately to windings about the rim along slots 90s and 90t, wound in the same manner and direction as the windings about the rim along slots 90g and 90h. Finally, a coupling segment 104 of wire 94 is formed arcuately along the remainder of the outer rim, extending to a point near slot 90a, thus encompassing substantially the circumference of the outer rim before returning to a terminal 106.

Figure 6:
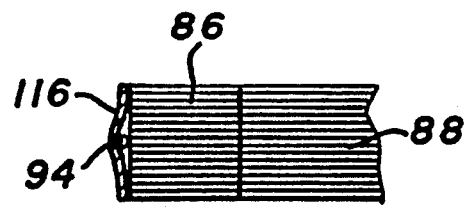
FIG. 6 is a sectional view taken along the line 6—6 in FIG. 4.

Thus, copper wire 94 is formed into four toroidal windings or active segments or sets of wire coils 108, 110, 112 and 114 spaced arcuately 90° from one another, and arcuate coupling segments 98, 100, 102 and 104 between the active segments. The coupling segments are shown radially outward of the outer rim for convenient illustration, but actually lie against the rim as shown in FIG. 6. The active segments are equally, angularly spaced about the outer rim, each occupying two of slots 90, i.e. including two wire coils. The four active segments correspond to the four poles of permanent magnet 40. The alternating and opposite toroidal directions in which successive active segments are wound corresponds to the alternate and opposite arrangement of the magnetic poles. Accordingly, induced voltages from the alternating N-magnetic and S-magnetic poles of permanent magnet 40 accumulate or are summed in series.

Four lengths of insulative tape, illustrated respectively at 116, 118, 120 and 122, are applied to the outwardly facing axial surface of outer rim 86 following assembly of wire 94 onto the rim. Each length of tape insulates copper wire 94, particularly along one of the coupling segments (FIG. 6), from subsequently applied copper wires. The pieces of tape are shown spaced apart from the outer rim for convenience in illustration, but actually are applied directly to the outer surface.

FIG. 7 illustrates a second stage in the assembly of stator 26, in which a copper wire 124 is wound in toroidal fashion about outer rim 86 to form four active segments 126, 128, 130 and 132, similar to the segments formed along copper wire 94 but angularly offset to run along slots 90c and 90d, 90i and 90j, 90o and 90p, and 90u and 90v, respectively. Copper wire 124 further includes coupling segments 134, 136, 138 and 140 between the active segments, which after assembly are insulated by respective lengths of tape 142, 144, 146 and 148 in the manner described in connection with the first assembly stage. Wire 124 is connected between terminals 150 and 152. Consecutive active segments are wound in opposite toroidal directions to correspond to the alternating opposite arrangement of the poles of the permanent magnet.

The final stage in the assembly of stator 26 is illustrated in FIG. 8. A copper wire 154 is wound in toroidal fashion about outer rim 86 to form four active segments 156, 158, 160 and 162, similar to the segments formed in copper wires 94 and 124, but once again angularly offset from the active segments of these other wires. In particular, the active segments run along slots 90e and 90f, 90k and 90l, 90q and 90r, and 90w and 90x, respectively. The wire includes coupling segments 164, 166, 168 and 170 running arcuately between the active segments. Following the winding of wire 154, the coupling segments are covered by respective lengths of insulative tape 172, 174, 176 and 178 as described in connection with previous stages. Once again, consecutive active segments are wound in opposite toroidal directions corresponding to the alternating opposite arrangement of the poles of permanent magnet 40. Wire 154 is connected to terminals 180 and 182.

Thus, three separate electrically conductive paths, electrically isolated from one another, are formed about the stator frame outer rim, by copper wires 94, 124, and 154, respectively. Each corresponds to one of three phases of the motor formed by the stator and rotor, spaced 120° apart in rotation. Each wire is formed into four active or toroidally coiled segments, corresponding to the four poles 76-82 of permanent magnet 40. The total number of segments is the product of the number of segments per wire times the number of wires, i.e. twelve. While the conductive paths could be applied as printed coil laminations or other suitable means, the presently preferred conductive paths are copper wires.

Preferably the number of teeth 88 (and slots 90) is an integral multiple of the total number of active segments. In this event the slots and teeth form a convenient guide for the angular positioning of each of the toroidal windings, with teeth 88 separating adjacent windings from one another. For stator 26 wound for three phases, twelve teeth and slots would suffice. Twenty-four teeth are provided, however, to provide additional and more closely spaced apart radially directed flux carrying material, for a smoother performance of the motor.

Following winding of wires 94, 124 and 154, Hall effect semiconductor element 68, and two further Hall effect semiconductor elements 184 and 186 are mounted to teeth 88 as shown in FIG. 8, spaced apart angularly 60°. A similarly spaced apart and redundant set of Hall sensors may be provided as shown, if desired. Sensors 68, 184 and 186 are used as a transducing means to detect the angular position of stator 26 and rotor 32 with respect to one another, based on the strength and direction of the sensed magnetic field. More particularly, sensor 68 spans slot 90w, sensor 184 spans slot 90c and sensor 186 spans slot 90g. Thus, the Hall sensors are located to produce the commercial standard 120 phasing. The Hall effect sensors can be utilized to control a selectively sequenced switching between an electric power source and wires 94, 124 and 154 to drive rotor 32, and further can be used as a tachometer to indicate the rotational velocity of the rotor.

The conventional manner of winding wires on a stator core similar to frame 66 would be about teeth 88, for example from a selected slot arcuately along the top of the back iron, down through a slot of opposite polarity, and arcuately along the bottom of the back iron to return to the original slot. In this winding configuration, the arcuate portions of the wire are inactive, with the active segments positioned in the slots, a configuration which favors a stator core with an axial length substantially greater than its diameter. Thus, this winding scheme is inefficient when applied to the present stator frame 66, with a diameter substantially greater than its length, because the inactive segments of each wire are unduly high in proportion to the total length of each wire.

By contrast, when stator frame 66 is wound as described in connection with FIGS. 4-8, the length of the active segments in each wire is substantially greater than the length of the arcuate coupling segments by a factor of two to three, due to the number of toroidal windings or traverses of the conductive path along each of slots 90. The number of windings per slot is determined based on the desired operating voltage (at the design speed of 4000 rpm), in this case thirty windings per slot corresponding to twelve volts. Six volts, for example, would call for fifteen windings along each slot. Nonetheless, the proportion of active segment length to inactive segment length in each of the wires remains sufficiently high to supply an equivalent operating torque to the motor using much shorter wires as compared to conventionally wound coils. The reduced length in each wire reduces resistance, and thus reduces the ohmic heat generated by current carried in the wire. Reduced ohmic heat is particularly important in connection with body implantable devices, as excessive heat can harm blood or other bodily fluids. The toroidal winding yields active segments equivalent to those of a conventional winding about teeth 88, utilizing significantly shorter lengths of copper wire.

A further advantage of the toroidal winding scheme is its location on stator frame 66, about the outer rim or back iron 86, as opposed to surrounding teeth 88. With the conductive paths thus moved radially outward, ohmic heat generated in wires 94, 124 and 154 is more easily dissipated, as the wires are closer to the outer perimeter of the rotor casing to provide a shorter path for heat dissipation to bodily fluids. The complex overlapping required in conventional successive windings about teeth 88 is avoided, with the copper wire coils wound independently of one another and insulated from one another as explained above. The radially inward edges of teeth 88 can be accurately machined to provide an annular reference surface for attachment of stator frame 66 to the exterior of rotor casing 20. With the rotor casing and stator frame concentric, forces of the magnetic field tend to radially center rotor 32 with respect to both the casing and stator, thus setting a precise radial gap between the rotor and stator.

Because of the use of a saline fluid lubricant to support rotor 32 by hydrodynamic bearing action, and further due to the thickness of the rotor casing wall between the rotor and stator, the gap between the rotor and stator is approximately 0.1 inches, larger by an order of magnitude than a conventional gap in the absence of a casing or hydrodynamic bearing. The reduced efficiency occasioned by the need for this comparatively large a gap is overcome by the size (volume) of stator frame 66, together with the toroidal windings of the stator wires.

When an electrical current is supplied in a repeating sequence to wires 94, 124 and 154, a magnet field is generated for driving the rotor. Returning to FIG. 1, it can be seen that rotor 32 is held concentric with the stator by rotor guide 52 and the journal bearings, but is not allowed to become axially aligned. Rather, thrust bearing 54 is positioned to maintain the rotor slightly above or vertically offset from an axially centered or aligned position relative to the stator. Accordingly, the magnetic field and thrust bearing act upon rotor 32 in opposite axial directions, tending to stabilize the rotor in its vertically offset position for smooth, stable operation of the pump. By contrast, if rotor 32, and more particularly permanent magnet 40, were allowed to operate at the axially centered location, it would oscillate vertically under inertial forces, causing lip seal 64 to slide on impeller shaft 50, causing the lip seal to wear, increasing the likelihood of blood clot formation at the seal/shaft interface, and permitting blood to enter the rotor chamber by virtue of the pison action of the lip seal along the shaft.

These difficulties are avoided by positioning thrust bearing 54 to displace the magnet and rotor from the axially centered position. The axial force for stabilizing the rotor and magnet is slight, smaller by an order of magnitude than the axial coupling force required in the aforementioned earlier design in which the rotor was driven by axially coupled magnets.

FIG. 9 discloses an alternative embodiment approach in which a stator frame 187 is wound with two copper wires 188 and 190, corresponding to two phases, for use in connection with a rotor having a four pole permanent magnet. Wire 188 is wound about an outer rim or back iron 192 of the stator frame, in four active segments 194, 196, 198 and 200. The toroidal windings of successive active segments run in opposite directions as explained above in connection with FIGS. 4–8. Wire 190 is similarly wound about the back iron, with active segments 202, 204, 206 and 208 angularly positioned between the corresponding active segments of wire 188, and also wound in a sequence of opposite toroidal directions. Accordingly, the number of active segments of each wire equals the number of poles in the permanent magnet, and the number of wires equals the number of phases. In connection with both embodiments, however, it should be noted that the number of active segments can be any integral multiple of the number of poles in the permanent magnet, and the number of copper wires as well as wire coils likewise can be any integral multiple of the number of phases.

FIG. 10 is a schematic illustration of a brushless motor controller which can be employed to control the motor in driving pump 16. A controller 216, e.g. a Model IM-6000 controller available from Intelligent Motor Control Corporation, includes inputs biased to a positive voltage (+V) and to ground. The motor speed is controlled by a control voltage $V_c$ provided by a potentiometer including a contact 209 movable along a resistance 211 between terminals biased respectively at +7 volts and ground. Hall elements 58, 184 and 186 are powered by a supply within the controller including terminals at +7 volts and at ground. Circuitry within controller 216 uses the Hall sensor output signals to control the switched voltages applied to the stator windings, thus to control the speed of the motor in proportion to the applied control voltage $V_c$.

FIG. 11 diagrammatically illustrates pump 16 implanted as a centrifugal left ventricle assist pump. Two pressure transducers 210 and 212 sense blood pressure at the impeller chamber inlet and outlet, respectively. Signals representing these respective pressures are supplied to a comparator 214, which in turn supplies its output to controller 216. Comparator 214 and controller 216 are located on the left side of a broken line 218, i.e. outside of the body. The outputs of Hall effect sensors 168, 184 and 186 are provided to controller 216, indicating the angular position of the rotor as well as its rotational velocity. A comparator 220 within controller 216 receives the Hall sensor tachometer output and the pressure differential output of comparator 214, and provides a velocity command whereby current supplied to stator wires 94, 124 and 154 is varied to alter the pump velocity. Thus, the velocity command is used in lieu of the potentiometer discussed in connection with controller 216 in FIG. 10.

The position signal of the Hall effect sensors is used to control switching circuitry in controller 216 which selectively connects a power supply in the controller to wires 94, 124 and 154 in a predetermined sequence to properly drive the rotor. A syringe pump 226 or other suitable means supplies a saline fluid lubricant to pump 16 over a fluid line 228 at a constant rate as described in the aforementioned U.S. Pat. No. 4,927,407. Thus, in response to a pressure difference signal indicating an increased demand for blood circulation, the rotational speed of the rotor and impeller may be increased to circulate blood at the higher demand rate. When the pressure differential signal indicates that the temporary increased need has subsided, the power supplied to the pump is reduced to its previous level.

Alternative approaches are available for controlling the rotational velocity of pump 16 in response to the signals provided by transducers 210 and 212. In one approach, the power supply can be a fixed DC supply, with the duty cycle of the high frequency switching among wires 94, 124 and 154 providing an "effective" DC voltage to these wires that varies in proportion to the fixed voltage, based on the duty cycle. Alternatively, the power supply may be a variable DC voltage, with the control circuitry being restricted to the commutating function.

Thus, in accordance with the present invention, a radially magnetically coupled rotor and stator provide an effective motor for rotating the impeller of a centrifugal pump at high speeds, configured to minimize ohmic heat generated in the stator windings and to facilitate dissipation of the ohmic heat generated. The interconnection of the rotor and stator is entirely through the magnetic field between them which passes through the dielectric rotor casing, thus preserving the hermetic seal of the pump for sterile integrity of the pump, as well as protection of the environment around the pump.

What is claimed is:

1. A pump drive motor, including:
   a rotor assembly including a permanent magnet having an equal number of N-magnetic and S-magnetic poles in an alternating configuration with opposite poles adjacent one another;
   a support means for rotatably supporting said rotor assembly;
   a stator including an annular stator frame coaxial with said rotor and fixed to said support means to provide a predetermined gap between said stator frame and said rotor assembly, said stator frame constructed of a magnetic flux carrying material and including an annular outer rim having a diameter greater than its axial length;
   said stator further including at least two electrical conductors disposed along said outer rim and electrically isolated from one another, each of said conductors formed into a series of active segments disposed symmetrically about said outer rim and coupling segments between said active segments, each of said active segments including multiple traverses of the associated conductor toroidally around said rim, each of said coupling segments running generally arcuately along said rim, said active segments having a length substantially greater than the length of said coupling segments, and with the active segments of each conductor selectively spaced apart angularly from the active segments of each of the other conductors; and
   a drive means including an electrical power supply, for providing an electrical current to said conductors in a predetermined sequence to rotate said rotor assembly relative to said support means and said stator.

2. The motor of claim 1 wherein:
   said stator surrounds said rotor assembly in radially spaced apart and approximately axially aligned relation thereto, to provide for a radial coupling of said rotor assembly and said stator.

3. The motor of claim 2 wherein:
   said stator frame further includes a plurality of teeth projected radially inwardly of said outer rim and spaced apart from one another to define a plurality of slots, with said active segments of said conductors disposed along said slots, the number of said slots being an integral multiple of the total number of said active segments.

4. The motor of claim 3 wherein:
   each of said teeth has a radially inward edge surface, with the edge surfaces of said teeth cooperating to define a reference surface of said stator frame contiguous with said support means.

5. The motor of claim 3 wherein:
   said stator frame comprises a laminar construction of at least ten silicone steel sheets, each sheet having a thickness, in the axial direction, of less than 0.02 inches.

6. The motor of claim 2 wherein:
   the number of conductors is an integral multiple of the number of phases, and each of said conductors has the same number of active segments, with the number of active segments in each conductor being an integral multiple of the number of poles in said permanent magnet.

7. The motor of claim 6 wherein:
   each of said conductors is an insulated metallic wire, and the active segments of each wire are comprised of toroidal windings in opposite directions about said outer rim.

8. The motor of claim 2 wherein:
   said support means comprises a dielectric casing defining a rotor chamber containing said rotor assembly, and further defining a fluid port open to said rotor chamber and to the exterior of said casing for receiving a fluid lubricant into said rotor chamber, the hydrodynamic bearing action of said fluid lubricant supporting said rotor assembly rotatably with respect to said casing, said predetermined gap between said rotor and said stator frame being of a size to accommodate the casing and allow sufficient flow of said fluid lubricant between said rotor and said casing for said hydrodynamic bearing action.

9. The motor of claim 8 wherein:
   said permanent magnet of the rotor assembly tends to seek an axially centered position with respect to said stator, and said casing includes a thrust bearing acting axially upon said rotor assembly to position and maintain said magnet slightly axially offset from said centered position.

10. The motor of claim 2 wherein:
    said magnet is annular and has four poles.

11. The motor of claim 1 further including:
    a detecting means for sensing the angular position of said rotor assembly with respect to said stator, and a switching means, responsive to said detecting means, for selectively coupling said conductors with said electrical power supply in accordance with said predetermined sequence.

12. The motor of claim 11 wherein:
said electrical power supply is a variable direct current power supply.
13. The motor of claim 11 wherein:
said power supply provides a fixed voltage, and effective voltages, less than the fixed voltage, are supplied to said conductors by a variable duty cycle of said switching means operating in a high frequency switching mode.

* * * * *